(12) United States Patent
Kocsis et al.

(10) Patent No.: US 6,310,009 B1
(45) Date of Patent: Oct. 30, 2001

(54) LUBRICATING OIL COMPOSITIONS CONTAINING SALIGENIN DERIVATIVES

(75) Inventors: Jody A. Kocsis, Chagrin Falls; James P. Roski, Wickliffe; Virginia A. Carrick, Chardon; Richard A. Denis, Auburn Township, Lake County; Thomas J. Wolak, Mentor, all of OH (US); Gordon D. Lamb, Mickleover (GB); Paul E. Adams, Willoughby Hills, OH (US); William D. Abraham, South Euclid, OH (US); Susan V Cowling, Painesville, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/761,400

(22) Filed: Jan. 16, 2001

Related U.S. Application Data (60) Provisional application No. 60/194,136, filed on Apr. 3, 2000.

(51) Int. Cl.[7] ............................................... C10M 129/10
(52) U.S. Cl. ........................ 508/186; 508/578; 508/584; 508/585; 508/586
(58) Field of Search ............................ 508/186, 391, 508/433, 438, 460, 578, 584, 585, 586

(56) References Cited

U.S. PATENT DOCUMENTS

| | | | |
|---|---|---|---|
| 2,250,188 | 7/1941 | Wilson | 252/39 |
| 2,647,873 | 8/1953 | Matthews et al. | 252/42.7 |
| 3,256,183 | 6/1966 | Greenwald | 252/32.7 |
| 4,053,428 | 10/1977 | Pindar et al. | 252/52 |
| 4,701,354 * | 10/1987 | Kitamura et al. | 427/255.6 |
| 4,916,031 * | 4/1990 | Kitamura et al. | 428/626 |
| 5,240,624 | 8/1993 | Koch | 252/49.6 |
| 5,259,967 | 11/1993 | Ripple | 252/32.007 |
| 5,371,140 * | 12/1994 | Parks | 525/54.42 |
| 5,378,791 | 1/1995 | Lancaster et al. | 528/137 |
| 5,516,441 | 5/1996 | Denis | 252/42.7 |
| 5,916,851 | 6/1999 | Hosonuma et al. | 508/363 |
| 6,103,672 * | 8/2000 | Dunn et al. | 508/185 |

* cited by examiner

Primary Examiner—Jacqueline V. Howard
(74) Attorney, Agent, or Firm—David M. Shold; Michael F. Esposito

(57) ABSTRACT

A saligenin derivative such as the magnesium salt represented by the formula

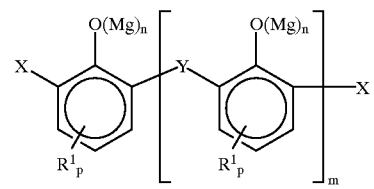

is useful as an additive for a lubricating composition. Preferably X is —CHO or —CH$_2$OH, and Y is —CH$_2$— or —CH$_2$OCH$_2$—. R$^1$ is a hydrocarbyl group containing 1 to 60 carbon atoms and m is 0 to 10. At least one aromatic ring should contain an R$^1$ substituent and the total number of carbon atoms in all R$^1$ groups should be at least 7.

36 Claims, 1 Drawing Sheet

Fig. 1

LUBRICATING OIL COMPOSITIONS CONTAINING SALIGENIN DERIVATIVES

CROSS-REFERENCE TO RELATED APPLICATIONS

This Application claims priority from U.S. Provisional Application Ser. No. 60/194,136, filed Apr. 3, 2000.

FIELD OF THE INVENTION

The present invention provides certain saligenin derivatives used in lubricating compositions. Heavy duty diesel engine oil formulations that contain, especially, borated or non-borated magnesium saligenin derivatives of the present invention exhibit significantly improved seal compatibility and reduced copper and lead corrosion. They also exhibit improved upper piston deposit performance, which can minimize excessive oil consumption and piston scuffing and can improve engine life.

BACKGROUND OF THE INVENTION

Saligenin, also known as salicyl alcohol and o-hydroxybenzyl alcohol, is represented by the structure

U.S. Pat. No. 2,250,188 (Wilson, Jul. 22, 1941) relates to mineral lubricating oils modified by addition of constituents to impart characteristics adapting them to conditions such as found in Diesel engines. In the lubricating oil is dissolved a small quantity of the calcium or other oil-soluble salt of the condensation product of formaldehyde with an alkyl phenol in which the alkyl group contains preferably 4 or 5 carbon atoms to insure oil solubility. Other metals than calcium, particularly the other alkaline earth metals and the light metals aluminum and zinc, may be employed in the formation of the oil-soluble metal salts.

U.S. Pat. No. 3,256,183 (Greenwald, Jun. 14, 1966) relates to lubricant compositions for use in engines of the diesel type, which include, among other components, an oil-soluble calcium phenate compound prepared by the process comprising the steps of reacting a mixture comprising 1 mole of an alkyl phenol and from about 1 to about 2 moles of a formaldehyde producing reagent in the presence of a catalyst at a temperature of from about 10° C. to about 99° C. and thereafter reacting said mixture with a calcium reagent selected from the class consisting of calcium hydroxide and calcium oxide at a temperature of at least about 30° C.

U.S. Pat. No. 5,516,441 (Denis, May 14, 1996) relates to a metal salt or boron compound of a hydrocarbyl-substituted aromatic hydroxy compound having at least two hydroxy-substituted aromatic rings bridged by sulfur, where at least one aromatic ring bears a substituent ortho to a hydroxy group, provides a useful lubricant additive. The substituent on the aromatic ring is an Δ-hydroxy aliphatic hydrocarbyl group or a —C(O)R² group, where R² is hydrogen or aliphatic hydrocarbyl. Reaction of aldehyde with the sulfur-coupled aromatic hydroxy compound should be conducted under non-condensing conditions. Preferred salts are magnesium.

SUMMARY OF THE INVENTION

The present invention provides a composition comprising a saligenin derivative represented by the formula wherein each X independently is —CHO, or —CH$_2$OH, each Y independently is —CH$_2$— or —CH$_2$OCH$_2$—, and wherein such —CHO groups comprise at least 10 mole percent of the X and Y groups;

each M is independently hydrogen, ammonium, or a valence of a metal ion;

each $R^1$ is independently a hydrocarbyl group containing 1 to 60 carbon atoms;

m is 0 to 10; and each p is independently 0, 1, 2, or 3;

provided that at least one aromatic ring contains an $R^1$ substituent and that the total number of carbon atoms in all $R^1$ groups is at least 7;

further provided that if m is 1 or greater, then one of the X groups can be —H.

The invention further provides a lubricating oil composition comprising a major amount of an oil of lubricating viscosity and a minor amount of the above saligenin derivative.

The invention further provides a process for preparing a saligenin derivative as above, particularly where M is magnesium, comprising combining a phenol substituted by said $R^1$ group with formaldehyde or a source of formaldehyde and magnesium oxide or magnesium hydroxide under reactive conditions, in the presence of a catalytic amount of a strong base; wherein the equivalent ratio of the substituted phenol to formaldehyde or source thereof is 1:1 to 1:4; whereby the saligenin derivative is formed such that X is at least in part —CHO and such —CHO groups comprise at least 10% of the X and Y groups.

DETAILED DESCRIPTION OF THE INVENTION

The present invention comprises a saligenin derivative which can be used as a component of a lubricating composition which comprises an oil of lubricating viscosity and, optionally, other additives.

Oil of Lubricating Viscosity

The diverse oils of lubricating viscosity include natural and synthetic lubricating oils and mixtures thereof. These lubricants include crankcase lubricating oils for spark-ignited and compression-ignited internal combustion engines, including automobile and truck engines, two-cycle engines, aviation piston engines, and marine and railroad diesel engines. They can also be used in gas engines, stationary power engines, and turbines. Automatic transmission fluids, transaxle lubricants, gear lubricants, metalworking lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils such as polymerized and interpolymerized olefins (e.g., polybutylenes, polypropylenes, propyleneisobutylene copolymers, poly(1-hexenes, poly(1-octenes), poly(1-decenes), and mixtures thereof); alkylbenzenes (e.g., dodecylbenzenes, tetradecylbenzenes, dinonylbenzenes, and di(2-ethylhexyl)-benzenes); polyphenyls (e.g., biphenyls, terphenyls, and alkylated polyphenyls), alkylated diphenyl ethers and alkylated diphenyl sulfides and the derivatives, analogs, and homologs thereof.

Alkylene oxide polymers and interpolymers and derivatives thereof where the terminal hydroxyl groups have been modified by esterification, etherification, or similar reaction constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1,000 diphenyl ether of polyethylene glycol having a molecular weight of 500–1,000, diethyl ether of polypropylene glycol having a molecular weight of 1,000–1,500) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, and alkenyl malonic acids) with a variety of alcohols (e.g., butyl alcohol, hexyl alcohol, dodecyl alcohol, 2-ethylhexyl alcohol, ethylene glycol, diethylene glycol monoether, and propylene glycol). Specific examples of these esters include dibutyl adipate, di(2-ethylhexyl sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, and tripentaerythritol.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except that they have been further treated in one or more purification steps to improve one or more properties. Many such purification techniques are known to those of skill in the art such a solvent extraction, acid or base extraction, filtration, percolation, or similar purification techniques. Rerefined oils are obtained by processes similar to those used to obtain refined oils which have been already used in service. Such rerefined oils are also known as reclaimed or reprocessed oils and often are additionally processed by techniques directed to removal of spent additives and oil breakdown products.

The aliphatic and alicyclic substituents, as well as aryl nuclei, are generally described as "hydrocarbon-based". The meaning of the term "hydrocarbon-based" as used herein is apparent from the following detailed discussion of "hydrocarbon-based substituent."

As used herein, the terms "hydrocarbon-based substituent," "hydrocarbyl substituent" or "hydrocarbyl group," which are used synonymously, are used in their ordinary sense, which is well-known to those skilled in the art. Specifically, any of these terms refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

Preferably, the hydrocarbon-based substituents in the compositions of this invention are free from acetylenic unsaturation. Ethylenic unsaturation, when present, preferably will be such that no more than one ethylenic lineage will be present for every 10 carbon-to-carbon bonds in the substituent. The hydrocarbon-based substituents are usually hydrocarbon in nature and more usually, substantially saturated hydrocarbon. As used in this specification and the appended claims, the word "lower" denotes substituents or groups containing up to seven carbon atoms; for example, lower alkoxy, lower alkyl, lower alkenyl, lower aliphatic aldehyde.

(A) The Saligenin Derivative

The saligenin derivative of the present invention can be represented by the formula where M is hydrogen, ammonium, or a valence of a metal ion, and the identity, description, and amounts of other symbols are as described below. Generally speaking if M is a metal it is not particularly limited but can be, for instance, an alkali metal such as lithium, sodium, or potassium; an alkaline earth metal such as magnesium, calcium, or barium; and other metals such as copper, zinc, and tin, or mixtures thereof. Ammonium ions can be the unsubstituted ammonium ion, $NH_4^+$ or amine ions in which one or more of the hydrogens are replaced by hydrocarbyl groups. Preferably M is calcium or magnesium, most preferably magnesium.

The preferred magnesium salt can be represented more particularly by the formula In this embodiment, (Mg) represents a valence of a magnesium ion. (Other valences of the normally divalent Mg ion, not shown, can be satisfied by other anions or by association with additional —O⁻ functionality of the same or additional saligenin derivatives.) Each n is independently 0 or 1, provided that when n is 0, the Mg is replaced by H, that is, to form an unneutralized phenolic —OH group. The average value of n in the composition overall is typically 0.1 to 1.0. That is, the structure represents a partially or completely neutralized magnesium salt, a value of 1.0 corresponding to complete neutralization of each site by the divalent Mg ion. The compound contains one aromatic ring or a multiplicity of aromatic rings linked by "Y" groups, and also "X" groups. Since "m" can be 0 to 10, this means that the number of such rings will typically be 1 to 11, although it is to be understood that the upper limit of "m" is not a critical variable. Preferably m is 2 to 9, more preferably 3 to 8 or 4 to 6. If m is 1 or greater, then one of the X groups can be —H.

Most of the rings contain at least one $R^1$ substituent, which is a hydrocarbyl group, preferably an alkyl group, containing 1 to 60 carbon atoms, preferably 7 to 28 carbon atoms, more preferably 9 to 18 carbon atoms. Of course it is understood that $R^1$ will normally comprise a mixture of various chain lengths, so that the foregoing numbers will normally represent an average number of carbon atoms in the $R^1$ groups (number average). $R^1$ can be linear or branched. Each ring in the structure will be substituted with 0, 1, 2, or 3 such $R^1$ groups (that is, p is 0, 1, 2, or 3), most typically 1, and of course different rings in a given molecule may contain different numbers of such substituents. At least one aromatic ring in the molecule must contain at least one $R^1$ group, and the total number of carbon atoms in all the $R^1$ groups in the molecule should be at least 7, preferably at least 12.

In the above structure the X and Y groups may be seen as groups derived from formaldehyde or a formaldehyde source, by condensative reaction with the aromatic molecule. While various species of X and Y may be present in the molecules in question, the commonest species comprising X are —CHO (aldehyde functionality) and —CH₂OH (hydroxymethyl functionality); similarly the commonest species comprising Y are —CH₂— (methylene bridge) and —CH₂OCH₂— (ether bridge). The relative molar amounts of these species in a sample of the above material can be determined by $^1H/^{13}C$ NMR as each carbon and hydrogen nucleus has a distinctive environment and produces a distinctive signal. (The signal for the ether linkage, —CH₂OCH₂— must be corrected for the presence of two carbon atoms, in order to arrive at a correct calculation of the molar amount of this material. Such a correction is well within the abilities of the person skilled in the art.)

In a preferred embodiment, X is at least in part —CHO and such —CHO groups comprise at least 10, 12, or 15 mole percent of the X and Y groups. Preferably the —CHO groups comprise 20 to 60 mole percent of the X and Y groups and more preferably 25 to 40 mole percent of the X and Y groups.

In another embodiment, X is at least in part —CH₂OH and such —CH₂OH groups comprise 10 to 50 mole percent of the X and Y groups, preferably 15 to 30 mole percent of the X and Y groups.

In an embodiment in which m is non-zero, Y is at least in part —CH₂— and such —CH₂— groups comprise 25 to 55 mole percent of the X and Y groups, preferably 32 to 45 mole percent of the X and Y groups.

In another embodiment Y is at least in part —CH₂OCH₂— and such —CH₂OCH₂— groups comprise 5 to 20 mole percent of the X and Y groups, and preferably 10 to 16 mole percent of the X and Y groups.

The relative amounts of the various X and Y groups depends to a certain extent on the conditions of synthesis of the molecules. Under many conditions the amount of —CH₂OCH₂— groups is relatively small compared to the other groups and is reasonably constant at about 13 to 17 mole percent. Ignoring the amount of such ether groups and focusing on the relative amounts of the —CHO, —CH₂OH, and —CH₂— groups, it has been found that particularly preferred compositions have the following relative amounts of these three groups, the total of such amounts in each case being normalized to equal 100%:

| | |
|---|---|
| —CHO: | 15–100%, preferably 20–60%, most preferably 25–50% |
| —CH₂OH: | 0–54%, preferably 4–46%, most preferably 10–40% |
| —CH₂: | 0–64%, preferably 18–64%, most preferably 20–60% |

Figure 1:
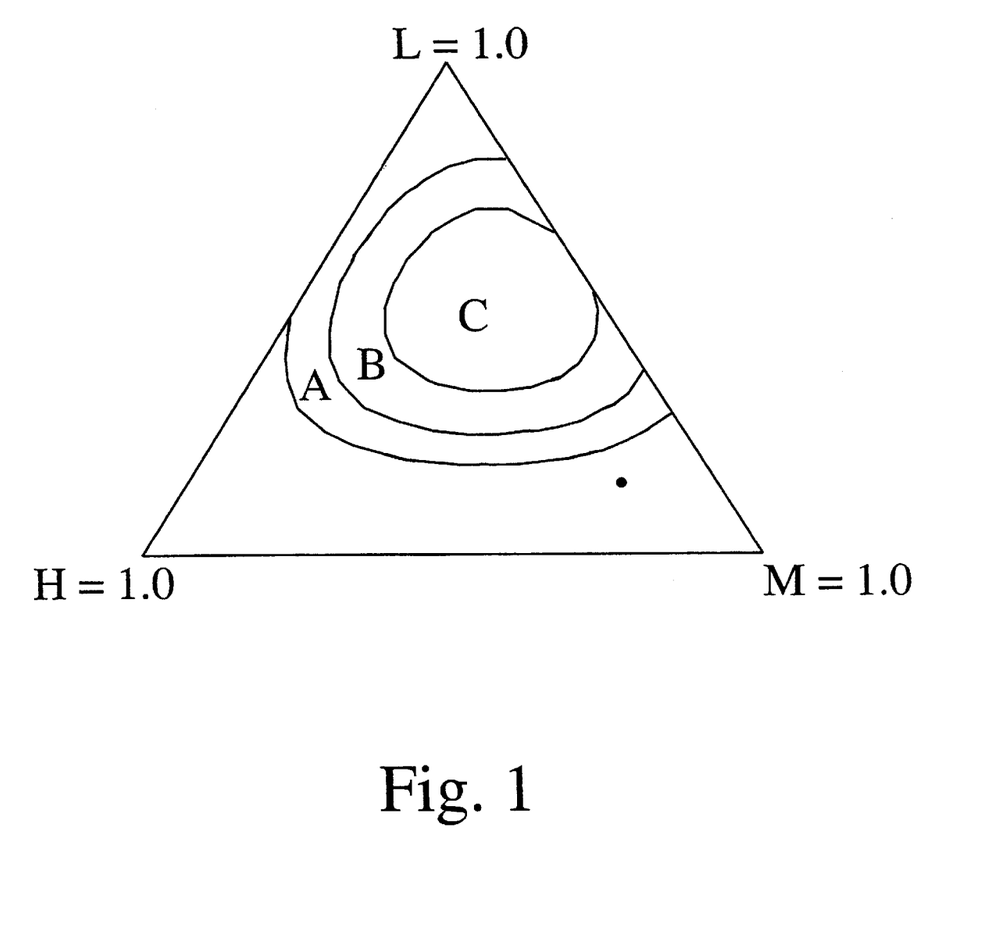
FIG. 1 is a triangular composition plot showing preferred compositions of the saligenin component in terms of relative amounts of three of its X and Y substituents, —CHO, —CH$_2$OH, and —CH$_2$—.

Alternatively preferred proportions can be taken from the triangular composition diagram shown in FIG. 1. In this diagram, vertex L represents a composition containing 100% aldehyde functionality (normalized as above), vertex H represents a composition containing 100% hydroxymethyl functionality, and vertex M represents a composition containing 100% methylene functionality. A generally preferred group of compositions of the present invention fall within the area designated "A," more preferred compositions fall within the area designated "B," and highly preferred compositions fall within the area designated "C." For comparative purposes, a dot (●) located in the lower right corner of the triangle represents a typical (comparative) composition of a conventional calcium phenol-formaldehyde reaction product.

The above-described compound is preferably a magnesium salt and, indeed, the presence of magnesium during the preparation of the condensed product is believed to be important in achieving the desired ratios of X and Y components described above. (After preparation of the compound, the Mg metal can be replaced by hydrogen, other metals, or ammonium if desired, by known methods.) The number of Mg, ions in the composition is characterized by an average value of "n" of 0.1 to 1.0, preferably 0.2 or 0.4 to 0.9, and more preferably 0.6 to 0.8, which correspond to 20–100%, 20 or 40–90%, or 60–80% neutralization by Mg. Since Mg is normally a divalent ion, it can neutralize up to two phenolic hydroxy groups. Those two hydroxy groups may be on the same or on different molecules. If the value of n is less than 1.0, this indicates that the hydroxy groups are less than completely neutralized by Mg ions. Alternatively, each Mg ion could be associated with one phenolic anion and an ion of another type such as a hydroxy ($OH^{31}$) ion or carbonate ion ($CO_3^-$), while still providing an n value of 1.0. The specification that the average value of n is 0.1 to 1.0 is not directly applicable to overbased versions of this material (described below and also a part of the present invention) in which an excess of Mg or another cation can be present. It should be understood that, even in an overbased material, some fraction of the phenolic OH groups may not have reacted with the magnesium and may retain the OH structure.

It is understood that in a sample of a large number of molecules, some individual molecules will exist which deviate from these parameters: for instance, there may be some molecules containing no $R^1$ groups whatsoever. Likewise, some fraction of molecules may contain only one (or even zero) X groups, while some may contain more than two X groups. And some fraction of the aromatic groups may be linked by Y groups to more than two neighboring aromatic groups. These molecules could be considered as impurities, and their presence will not negate the present invention so long as the majority (and preferably the substantial majority) of the molecules of the composition are as described. In any event, compositions exhibiting this type of variability are to be construed as encompassed by the present invention and the description that a material is "represented by" the formula shown. There is believed to be a reasonable possibility that a significant fraction of the polynuclear molecules of the present invention may bear only a single X group. In order to explicitly account for this possibility, it is to be understood that in the materials of an embodiment of the present invention, if m is 1 or greater, one (but preferably not both) of the X groups in the above structures can be —H.

The above-described component can be prepared by combining a phenol substituted by the above-described $R^1$ group with formaldehyde or a source of formaldehyde and magnesium oxide or magnesium hydroxide under reactive conditions, in the presence of a catalytic amount of a strong base.

Substituted phenols, and alkyl-substituted phenols in particular, are well known items of commerce. Alkylated phenols are described in greater detail in U.S. Pat. No. 2,777,874.

Formaldehyde and its equivalents are likewise well known. Common reactive equivalents of formaldehyde includes paraformaldehyde, trixoane, formalin and methal. For convenience, paraformaldehyde is preferred.

The relative molar amounts of the substituted phenol and the formaldehyde can be important in providing products with the desired structure and properties. It is preferred that the substituted phenol and formaldehyde are reacted in equivalent ratios of 1:1 to 1:3 or 1:4, more preferably 1:1.1 to 1:2.9 or 1:1.4 to 1:2.6., and still more preferably 1:1.7 to 1:2.3. Thus under preferred conditions there will be about a 2:1 equivalent ratio of formaldehyde. (One equivalent of formaldehyde is considered to correspond to one $H_2CO$ unit; one equivalent of phenol is considered to be one mole of phenol.) The strong base is preferably sodium hydroxide or potassium hydroxide, and can be supplied in an aqueous solution.

The process can be conducted by combining the above components with an appropriate amount of magnesium oxide or magnesium hydroxide with heating and stirring. A diluent such as mineral oil or other diluent oil can be included to provide for suitable mobility of the components. An additional solvent such as an alcohol can be included if desired, although it is believed that the reaction may proceed more efficiently in the absence of additional solvent. The reaction can be conducted at room temperature or, preferably, a slightly elevated temperature such as 35–120° C., 70–110° C., or 90–100° C., and of course the temperature can be increased in stages. When water is present in the reaction mixture it is convenient to maintain the mixture at or below the normal boiling point of water. After reaction for a suitable time (e.g., 30 minutes to 5 hours or 1 to 3 hours) the mixture can be heated to a higher temperature, preferably under reduced pressure, to strip off volatile materials. Favorable results are obtained when the final temperature of this stripping step is 100 to 150° C., preferably 120 to 145° C.

Reaction under the preferred conditions described above leads to a product which has a relatively high content of —CHO substituent groups, that is, 10%, 12%, 15%, or greater. Such materials, when used as detergents in lubricating compositions, exhibit good upper piston cleanliness performance, low Cu/Pb corrosion, and good compatibility with seals. Use of metals other than magnesium in the synthesis typically leads to a reduction in the content of —CHO substituent groups.

EXAMPLE 1

To a 5-L, 4-necked round bottom flask equipped with stirrer, stopper, thermowell, and reflux condenser, the following are charged: 670 g diluent oil (mineral oil), 1000 g dodecyl phenol, and a solution of 3 g NaOH in 40 g water. The mixture is heated to 35° C. with stirring (350 r.p.m.). When 35° C. is attained, 252 g of paraformaldehyde (90%) are added to the mixture and stirring is continued. After 5 minutes, 5 g of MgO and 102 g of additional diluent oil are added. The mixture is heated to 79° C. and held at temperature for 30 minutes. A second increment of 58 g MgO is added and the batch further heated and maintained at 95–100° C. for 1 hour. Thereafter the mixture is heated to 120° C. under a flow of nitrogen at 28 L/hr (1.0 std. $ft^3$/hr.). When 120° C. is reached, 252 g diluent oil is added, and the mixtures is stripped for 1 hour at a pressure of 2.7 kPa (20 torr) at 120° C. for 1 hour and then filtered.

The resulting product is analyzed and contains 1.5% by weight magnesium and has a Total Base Number (TBN) of 63. Analysis of the product by 1D and 2D $^1H/^{13}C$ NMR reveals an aldehyde content of 29 mole %, a methylene bridge content of 38 mole %, an ether bridge content of 12 mole %, and a hydroxymethyl content of 21 mole %.

EXAMPLE 2

Comparative

Example 1 is substantially repeated except that $Ca(OH)_2$ replaces the MgO and no catalytic NaOH is employed. After stripping under a nitrogen flow at 150° C. and isolation by filtration, the resulting product is analyzed and determined to contain 14 mole % aldehyde functionality.

The material prepared by the above process can be further treated by boration or by overbasing. Borated compositions are prepared by reaction of the above-described saligenin derivative one or more boron compounds. Suitable boron compounds include boric acid, borate esters, and alkali or mixed alkali metal and alkaline earth metal borates. These metal borates are generally a hydrated particulate metal borate and they, as well as the other borating agents, are known in the art and are available commercially. Typically the saligenin derivative is heated with boric acid at 50–100° C. or 100–150° C.

EXAMPLE 3

Comparative—Prepared Without Strong Base

To a 5-L, 4-necked round bottom flask equipped with stirrer, stopper, thermowell, and reflux condenser, the following are charged: 670 g diluent oil (mineral oil), 1000 g dodecyl phenol, and 40 g water. The mixture is heated to 35° C. with stirring (350 r.p.m.). When 35° C. is attained, 170 g of paraformaldehyde (90%) are added to the mixture and stirring is continued. After 5 minutes, 5 g of MgO and 102 g of additional diluent oil are added. The mixture is heated to 79° C. and held at temperature for 30 minutes. A second increment of 58 g MgO is added and the batch further heated and maintained at 95–100° C. for 1 hour. After the 1 hour hold, 252 g diluent oil is added. Thereafter the mixture is heated to 150° C. under a flow of nitrogen at 28 L/hr (1.0 std. ft$^3$/hr.), held 1 hour, and then filtered.

The resulting product is analyzed and contains 0.4% by weight magnesium and has a Total Base Number (TBN) of 22. Analysis of the product by 1D and 2D $^1$H/$^{13}$C NMR reveals an aldehyde content of 6 mole %, a methylene bridge content of 88 mole %, an ether bridge content of 2 mole %, and a hydroxymethyl content of 4 mole %.

EXAMPLE 4

To a 5-L, 4-necked round bottom flask equipped with stirrer, stopper, thermowell, and reflux condenser, the following are charged: 1466 g toluene, 1600 g dodecyl phenol, and a solution of 10 g of a 50/50 mixture of NaOH and water. The mixture is heated to 35° C. with stirring (350 r.p.m.). When 35° C. is attained, 403 g of paraformaldehyde (90%) are added to the mixture and stirring is continued. After 5 minutes, 8 g of MgO is added. The mixture is heated to 79° C. and held at temperature for 30 minutes. A second increment of 93 g MgO is added and the batch is heated to 80° C. for 1 hour. Thereafter the mixture is heated to 80° C. and held for 1 hr and thereafter the mixture is filtered.

The resulting product is analyzed and contains 2.4% by weight magnesium and has a Total Base Number (TBN) of 99. Analysis of the product by 1D and 2D $^1$H/$^{13}$C NMR reveals an aldehyde content of 16 mole %, a methylene bridge content of 7 mole %, an ether bridge content of 9 mole %, and a hydroxymethyl content of 68 mole %.

EXAMPLE 5

Borated material

To a 5-L, 4-necked round bottom flask equipped with stirrer, stopper, thermowell, and reflux condenser, the following are charged: 356 g of the product of Example 1, 100 g toluene, and 11.4 g H$_3$BO$_3$. The mixture is heated to 80° C. with stirring at 350 r.p.m. and maintained at temperature for 30 minutes. Thereafter the mixture is heated to 100° C. and held at temperature for 2–4 hours. The mixture is stripped of volatiles for 1 hour at a pressure of 2.7 kPa (20 torr) at 120° C. and then filtered.

The resulting product is analyzed and contains 1.4% by weight magnesium, 0.3% by weight boron, and has a Total Base Number (TBN) of 63. Analysis of the product by 1D and 2D $^1$H/$^{13}$C NMR reveals an aldehyde content of 27 mole %, a methylene bridge content of 38 mole %, an ether bridge content of 13 mole %, and a hydroxymethyl content of 22 mole %.

The material can also be overbased. Overbased salts of organic acids are widely known to those of skill in the art and generally include metal salts wherein the amount of metal present in them exceeds the stoichiometric amount. Such salts are said to have conversion levels in excess of 100% (i.e., they comprise more than 100% of the theoretical amount of metal needed to convert the acid to its "normal" or "neutral" salt). They are commonly referred to as overbased, hyperbased or superbased salts and are usually salts of organic sulfur acids, organic phosphorus acids, carboxylic acids, phenols or mixtures of two or more of any of these. As a skilled worker would realize, mixtures of such overbased salts can also be used.

The terminology "metal ratio" is used in the prior art and herein to designate the ratio of the total chemical equivalents of the metal in the overbased salt to the chemical equivalents of the metal in the salt which would be expected to result in the reaction between the organic acid to be overbased and the basically reacting metal compound according to the known chemical reactivity and stoichiometry of the two reactants. Thus, in a normal or neutral salt the metal ratio is one and, in an overbased salt, the metal ratio is greater than one. The overbased salts used as component (A) in this invention usually have metal ratios of at least 1.2:1 or 1.4:1. Often they have ratios of at least 2:1 or 4:1. Usually they have metal ratios not exceeding 20:1. Typically, salts having ratios of 1.5:1 to 15:1 are used.

When the material of the present invention is overbased, the stoichiometrically excess metal can be magnesium or it can be another metal or a mixture of cations. The basically reacting metal compounds used to make these overbased salts are usually an alkali or alkaline earth metal compound (i.e., the Group IA, IIA, and IIB metals excluding francium and radium and typically excluding rubidium, cesium and beryllium), although other basically reacting metal compounds can be used. Compounds of Ca, Ba, Mg, Na and Li, such as their hydroxides and alkoxides of lower alkanols are usually used as basic metal compounds in preparing these overbased salts but others can be used as shown by the prior art referred to herein. Overbased salts containing a mixture of ions of two or more of these metals or other cations, including mixtures of alkaline earth metals such as Mg and Ca, can be used in the present invention.

Overbased materials are generally prepared by reacting an acidic material (typically an inorganic acid or lower carboxylic acid, preferably carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter. The acidic organic compound will, in the present instance, be the above-described saligenin derivative.

The acidic material used in preparing the overbased material can be a liquid such as formic acid, acetic acid, nitric acid, or sulfuric acid. Acetic acid is particularly useful. Gaseous acidic materials can also be used, such as HCl, $SO_2$, $SO_3$, $CO_2$, or $H_2S$, preferably $CO_2$ or mixtures thereof, e.g., mixtures of $CO_2$ and acetic acid. The acidic material, which is preferably an acidic gas, is reacted with the mixture under conditions to react, normally, with the majority of, preferably 80–95% or 85–90% of, the stoichiometric excess of the metal base. Strongly acidic materials, however, would normally be used in an amount less than an equivalent of the phenol, while weakly acidic materials such as $CO_2$ can be used in excess.

A promoter is a chemical employed to facilitate the incorporation of metal into the basic metal compositions. The promoters are diverse and are well known in the art. A discussion of suitable promoters is found in U.S. Pat. Nos. 2,777,874, 2,695,910, and 2,616,904. These include the alcoholic and phenolic promoters, which are preferred. The alcoholic promoters include the alkanols of one to twelve carbon atoms such as methanol, ethanol, amyl alcohol, octanol, isopropanol, and mixtures of these. Phenolic promoters include a variety of hydroxy-substituted benzenes and naphthalenes. A particularly useful class of phenols are the alkylated phenols of the type listed in U.S. Pat. No. 2,777,874, e.g., heptylphenols, octylphenols, and nonylphenols. Mixtures of various promoters are sometimes used.

Patents specifically describing techniques for making basic salts of acidic organic compounds generally include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109.

EXAMPLE 6

Mg Saligenin Derivative Overbased With Ca

Into a 2 L four-necked flask equipped with stirrer, thermowell, reflux condenser, and a subsurface tube, is charged 1000 g of the product of Example 1 (Mg saligenin derivative in diluent oil), 50 g of a mixture of isobutyl and amyl alcohols, 100 g of methanol, and 74 g of $Ca(OH)_2$. A solution of 1 g acetic acid in 4 g water is added to the flask and the contents are held, with stirring, at 44° C. for 30 minutes. Carbon dioxide is blown through the mixture for 1 hour or longer, at 14 L/hr (0.5 std. $ft^3$/hr.) until a direct base number of 15 is obtained. The mixture is heated to 120° C. under a nitrogen flow of 28 L/hr (1.0 std. $ft^3$/hr.) for 1 hour, to strip volatiles. The resulting mixture is filtered and determined to have a TBN of 142 and to contain 3% Ca and 1.4% Mg by weight. NMR analysis reveals 30% aldehyde functionality, 39% methylene coupling, 17% ether coupling, and 14% hydroxymethyl functionality.

EXAMPLE 7

Into a 3 L four-necked flask equipped as in Example 6 is charged 100 g of the product of Example 1, 50 g of a mixture of isobutyl and amyl alcohols, and 111 g $Ca(OH)_2$. The mixture is heated to 50° C. and a solution of 159 g of stearic acid and 150 g diluent oil are added. The mixture is heated to 70° C. and maintained at temperature for 30 minutes, then cooled to 60° C. To the mixture is added 100 g of methanol and 10 g acetic acid. Carbon dioxide is blown through the mixture for 1 hour or longer at 28 L/hr (1.0 std. $ft^3$/hr.) to a direct base number of 15. A second increment of $Ca(OH)_2$, 111 g, is added and carbon dioxide is similarly blown through the mixture to a direct base number of 15. The mixture is stripped at 120° C. under a nitrogen flow of 28 L/hr (1.0 std. $ft^3$/hr.) and maintained at temperature for 1 hour. The product is filtered and exhibits a TBN of 234, containing 7% Ca and 1% Mg. Analysis reveals 31% aldehyde functionality, 39% methylene coupling, 18% ether coupling, and 12% hydroxymethyl functionality.

EXAMPLE 8

Mg Overbased Saligenin Derivative

Into a 2-liter, four-necked flask equipped with stirrer, thermowell, reflux condenser, and subsurface tube, is charged 1000 g of the product of example 1, 50 g of a mixture of isobutyl and amyl alcohols, and 63 g MgO. The mixture is heated, with stirring, to 50° C. A solution of 130 g of stearic acid and 100 g of dil oil is added. The mixture is heated to 70° C. and held at this temperature for 3 hours. The mixture was cooled to 60° C. To the mixture, 100 g of methanol and 7 g acetic acid are added. Carbon dioxide is blown through the mixture for over 3 hours at 28 L/hr (0.5 std. $ft^3$/hr) until a direct base number of less than 5 is obtained for the mixture. The mixture is stripped to 120° C. under a carbon dioxide flow of 28 L/hr (0.5 std. $ft^3$/hr) and held at this temperature for 1 hour under nitrogen flow at 14 L/hr (0.5 std. $ft^3$/hr.). The product is filtered and determined to have a TBN of 130 and to contain 2.8 weight % magnesium. Analysis reveals 32% aldehyde functionality, 41% methylene coupling, 12% ether coupling, and 15% hydroxymethyl functionality.

The overbased material can also be borated by reaction with a borating agent in a known manner, as briefly described above.

The Mg saligenin derivative can be incorporated into the lubricant along with other components in any order. It can be blended along with the other components or it can be added afterwards as a top-treatment.

In another embodiment, a lubricating oil composition containing the magnesium saligenin derivative may contain one or more additional components including, typically, at least one of the following:

(B) a metal overbased composition (other than the overbased material described above)

(C) a dispersant, (D) a metal salt represented by the formula, and (E) an antioxidant.

(B) The (Other) Metal Overbased Composition

Overbased compositions are well known, and the general process for preparing overbased compositions has been described in connection with the preparation of overbased Mg saligenin derivatives, above. The optional other overbased compositions can be prepared based on a variety of other well known organic acidic materials including sulfonic acids, carboxylic acids (including substituted salicylic acids), phenols, phosphonic acids, and mixtures of any two or more of these. These materials and methods for overbasing of them are well known from numerous U.S. Patents including those mentioned above in connection with the overbasing of the saligenin derivative and need not be further described in detail.

Preferred overbased materials include overbased phenates derived from the reaction of an alkylated phenol, preferably wherein the alkyl group has at least 6 aliphatic carbon atoms. The phenate is optionally reacted with an aldehyde such as formaldehyde or acetaldehyde, or an aldehyde-containing compound such as glyoxylic acid, or with a sulfurization agent, or mixtures thereof, to provide a bridged or linked structure.

Other preferred overbased materials include metal overbased sulfonates derived from an alkylated aryl sulfonic acid wherein the alkyl group has at least 15 aliphatic carbon atoms.

Other preferred overbased materials include metal overbased carboxylates derived from fatty acids having at least 8 aliphatic carbon atoms.

The preferred overbased materials may contain any of the metal components described above and mixtures thereof, but preferably an alkali metal or alkaline earth metal, more preferably calcium, magnesium, lithium or sodium.

The other, optional overbased material can also be borated (as can the overbased saligenin derivative) by treatment with a borating agent such as boric acid. Typical conditions include heating the basic metal salt with boric acid at 50 to 100° C. or 100 to 150° C., the number of equivalents of boric acid being roughly equal to or less than the number of equivalents of metal in the salt. U.S. Pat. No. 3,929,650 discloses borated complexes and their preparation.

(C) The Dispersant

Dispersants are well known in the field of lubricants and include primarily what are sometimes referred to as "ashless" dispersants because (prior to mixing in a lubricating composition) they do not contain ash-forming metals and they do not normally contribute any ash forming metals when added to a lubricant. Dispersants are characterized by a polar group attached to a relatively high molecular weight hydrocarbon chain.

One class of dispersant is Mannich bases. These are materials which are formed by the condensation of a higher molecular weight, alkyl substituted phenol, an alkylene polyamine, and an aldehyde such as formaldehyde. Such materials may have the general structure (including a variety of isomers and the like) and are described in more detail in U.S. Pat. No. 3,634,515.

Another class of dispersant is high molecular weight esters. These materials are similar to the above-described succinimides except that they may be seen as having been prepared by reaction of a hydrocarbyl acylating agent and a polyhydric aliphatic alcohol such as glycerol, pentaerythritol, or sorbitol.

Such materials are described in more detail in U.S. Pat. No. 3,381,022.

Other dispersants include polymeric dispersant additives, which are generally hydrocarbon-based polymers which contain polar functionality to impart dispersancy characteristics to the polymer.

A preferred class of dispersants is the carboxylic dispersants. Carboxylic dispersants include succinic-based dispersants, which are the reaction product of a hydrocarbyl substituted succinic acylating agent with an organic hydroxy compound or, preferably, an amine containing at least one hydrogen attached to a nitrogen atom, or a mixture of said hydroxy compound and amine. The term "succinic acylating agent" refers to a hydrocarbon-substituted succinic acid or succinic acid-producing compound. Such materials typically include hydrocarbyl-substituted succinic acids, anhydrides, esters (including half esters) and halides.

Succinic based dispersants have a wide variety of chemical structures including typically structures such as In the above structure, each $R^1$ is independently a hydrocarbyl group, preferably a polyolefin-derived group having an $\overline{M}n$ of 500 or 700 to 10,000, where $\overline{M}n$ is number average molecular weight. Typically the hydrocarbyl group is an alkyl group, frequently a polyisobutyl group with $\overline{M}n$ of 500 or 700 to 5000, preferably 1500 or 2000 to 5000. Alternatively expressed, the $R^1$ groups can contain 40 to 500 carbon atoms and preferably 50 to 300 carbon atoms, preferably aliphatic carbon atoms. The $R^2$ are alkenyl groups, commonly ethylenyl ($C_2H_4$) groups. Such molecules are commonly derived from reaction of an alkenyl acylating agent with a polyamine, and a wide variety of linkages between the two moieties is possible beside the simple imide structure shown above, including a variety of amides and quaternary ammonium salts. Succinimide dispersants are more fully described in U.S. Pat. No. 4,234,435.

The polyalkenes from which the substituent groups are derived are typically homopolymers and interpolymers of polymerizable olefin monomers of 2 to 16 carbon atoms; usually 2 to 6 carbon atoms.

The olefin monomers from which the polyalkenes are derived are polymerizable olefin monomers characterized by the presence of one or more ethylenically unsaturated groups (i.e., >C=C<); that is, they are mono-olefinic monomers such as ethylene, propylene, 1-butene, isobutene, and 1-octene or polyolefinic monomers (usually diolefinic monomers) such as 1,3-butadiene, and isoprene. These olefin monomers are usually polymerizable terminal olefins; that is, olefins characterized by the presence in their structure of the group >C=CH$_2$. Relatively small amounts of non-hydrocarbon substituents can be included in the polyolefin, provided that such substituents do not substantially interfere with formation of the substituted succinic acid acylating agents.

Each $R^1$ group may contain one or more reactive groups, e.g., succinic groups, thus being represented (prior to reaction with the amine) by structures such as in which y represents the number of such succinic groups attached to the $R^1$ group. In one type of dispersant, y=1. In another type of dispersant, y is greater than 1, preferably greater than 1.3 or greater than 1.4; and most preferably y is equal to or greater than 1.5. Preferably y is 1.4 to 3.5, especially is 1.5 to 3.5 and most especially 1.5 to 2.5.

Fractional values of y, of course, can arise because different specific $R^1$ chains may be reacted with different numbers of succinic groups.

The amines which are reacted with the succinic acylating agents to form the carboxylic dispersant composition can be monoamines or polyamines. In either case they will be characterized by formula $R^4R^5NH$ wherein $R^4$ and $R^5$ are each independently hydrogen, or hydrocarbon, amino-substituted hydrocarbon, hydroxy-substituted hydrocarbon, alkoxy-substituted hydrocarbon, amino, carbamyl, thiocarbamyl, guanyl, and acylimidoyl groups provided that only one of $R^4$ and $R^5$ is hydrogen. In all cases, therefore, they will be characterized by the presence within their structure of at least one H—N< group. Therefore, they have at least one primary (i.e., $H_2N$—) or secondary amino (i.e., H—N<) group. Examples of monoamines include ethylamine, diethylamine, n-butylamine, di-n-butylamine, allylamine, isobutylamine, cocoamine, stearylamine, laurylamine, methyllaurylamine, oleyl-amine, N-methyl-octylamine, dodecylamine, and octadecylamine.

The polyamines from which (C) is derived include principally alkylene amines conforming, for the most part, to the formula wherein t is an integer preferably less than 10, A is a hydrogen group or a hydrocarbyl group preferably having up to 30 carbon atoms, and the alkylene group is preferably an alkylene group having less than 8 carbon atoms. The alkylene amines include principally methylene amines, ethylene amines, hexylene amines, heptylene amines, octylene amines, other polymethylene amines. They are exemplified specifically by: ethylene diamine, triethylene tetramine, propylene diamine, decamethylene diamine, octamethylene diamine, di(heptamethylene) triamine, tripropylene tetramine, tetraethylene pentamine, trimethylene diamine, pentaethylene hexamine, di(-trimethylene) triamine. Higher homologues such as are obtained by condensing two or more of the above-illustrated alkylene amines likewise are useful. Tetraethylene pentamine is particularly useful.

The ethylene amines, also referred to as polyethylene polyamines, are especially useful. They are described in some detail under the heading "Ethylene Amines" in Encyclopedia of Chemical Technology, Kirk and Othmer, Vol. 5, pp. 898–905, Interscience Publishers, New York (1950).

Hydroxyalkyl-substituted alkylene amines, i.e., alkylene amines having one or more hydroxyalkyl substituents on the nitrogen atoms, likewise are useful. Examples of such amines include N-(2-hydroxyethyl)ethylene diamine, N,N'-bis(2-hydroxy-ethyl)-ethylene diamine, 1-(2-hydroxyethyl) piperazine, monohydroxypropyl)-piperazine, di-hydroxypropy-substituted tetraethylene pentamine, N-(3-hydroxypropyl)-tetra-methylene diamine, and 2-heptadecyl-1-(2-hydroxyethyl)-imidazoline.

Higher homologues, such as are obtained by condensation of the above-illustrated alkylene amines or hydroxy alkyl-substituted alkylene amines through amino radicals or through hydroxy radicals, are likewise useful.

The carboxylic dispersant composition (C), obtained by reaction of the succinic acid-producing compounds and the amines described above, may be amine salts, amides, imides, imidazolines as well as mixtures thereof. To prepare the carboxylic dispersant composition (C), one or more of the succinic acid-producing compounds and one or more of the amines are heated, optionally in the presence of a normally liquid, substantially inert organic liquid solvent/diluent at an elevated temperature, generally in the range of 80° C. up to the decomposition point of the mixture or the product; typically 100° C. to 300° C.

The succinic acylating agent and the amine (or organic hydroxy compound, or mixture thereof) are reacted in amounts sufficient to provide at least one-half equivalent, per equivalent of acid-producing compound, of the amine (or hydroxy compound, as the case may be). Generally, the maximum amount of amine present will be about 2 moles of amine per equivalent of succinic acylating agent. For the purposes of this invention, an equivalent of the amine is that amount of the amine corresponding to the total weight of amine divided by the total number of nitrogen atoms present. The number of equivalents of succinic acid-producing compound will vary with the number of succinic groups present therein, and generally, there are two equivalents of acylating reagent for each succinic group in the acylating reagents. Additional details and examples of the procedures for preparing the nitrogen-containing compositions of the present invention by reaction of succinic acid-producing compounds and amines are included in, for example, U.S. Pat. Nos. 3,172,892; 3,219,666; 3,272,746; and 4,234,435.

The dispersants may be borated in much the same way as the saligenin derivative or the other overbased material, described above. The dispersants may also be treated by reaction with maleic anhydride as described in PCT application US99/23940 filed Oct. 13 1999.

(C) The Metal Salt of a Phosphorus Acid Metal salts of the formula wherein $R^8$ and $R^9$ are independently hydrocarbyl groups containing 3 to 30 carbon atoms are readily obtainable by the reaction of phosphorus pentasulfide ($P_2S_3$) and an alcohol or phenol to form an O,O-dihydrocarbyl phosphorodithioic acid corresponding to the formula The reaction involves mixing at a temperature of 20° C. to 200° C., four moles of an alcohol or a phenol with one mole of phosphorus pentasulfide. Hydrogen sulfide is liberated in this reaction. The acid is then reacted with a basic metal compound to form the salt. The metal M, having a valence n, generally is aluminum, lead, tin, manganese, cobalt, nickel, zinc, or copper, and most preferably zinc. The basic metal compound is thus preferably zinc oxide, and the resulting metal compound is represented by the formula The $R^8$ and $R^9$ groups are independently hydrocarbyl groups that are preferably free from acetylenic and usually also from ethylenic unsaturation. They are typically alkyl, cycloalkyl, aralkyl or alkaryl group and have 3 to 20 carbon atoms, preferably 3 to 16 carbon atoms and most preferably up to 13 carbon atoms, e.g., 3 to 12 carbon atoms. The alcohol which reacts to provide the $R^8$ and $R^9$ groups can be a mixture of a secondary alcohol and a primary alcohol, for instance, preferably a mixture of isopropanol and 4-methyl-2-pentanol.

Such materials are often referred to as zinc dialkyldithiophosphates or simply zinc dithiophosphates. They are well known and readily available to those skilled in the art of lubricant formulation.

The amount of the metal salt of a phosphorus acid in a completely formulated lubricant, if present, will typically be 0.1 to 4 percent by weight, preferably 0.5 to 2 percent by weight, and more preferably 0.75 to 1.25 percent by weight. Its concentration in a concentrate will be correspondingly increased, to, e.g., 5 to 20 weight percent.

(E) The Antioxidant

In a further embodiment, the lubricating oil composition may also contain an antioxidant. Antioxidants for use in lubricant compositions are well known and include a variety of chemical types including phenate sulfides, phosphosulfurized terpenes, sulfurized esters, aromatic amines, and hindered phenols.

Aromatic amine are typically of the formula wherein $R^5$ is a phenyl group or a phenyl group substituted by $R^7$, and $R^6$ and $R^7$ are independently a hydrogen or an alkyl group containing 1 to 24 carbon atoms. Preferably $R^5$ is a phenyl group substituted by $R^7$ and $R^6$ and $R^7$ are alkyl groups containing from 4 to 20 carbon atoms. In one embodiment the antioxidant can be an alkylated diphenylamine such as nonylated diphenylamine of the formula

Hindered phenol antixoidants are typically alkyl phenols of the formula wherein $R^4$ is an alkyl group containing 1 up to 24 carbon atoms and a is an integer of 1 to 5. Preferably $R^4$ contains 4 to 18 carbon atoms and most preferably from 4 to 12 carbon atoms. $R^4$ may be either straight chained or branched chained; branched chained is generally preferred. The preferred value for a is an 1 to 4 and most preferred 1 to 3 or, particularly, 2. Preferably the phenol is a butyl substituted phenol containing 2 or 3 t-butyl groups. When a is 2, the t-butyl groups occupy the 2,6-position, that is, the phenol is sterically hindered:

A particularly preferred antioxidant is a hindered, ester-substituted phenol such as one represented by the formula and more preferably wherein $R^3$ is a straight chain or branched chain alkyl group containing 2 to 22 carbon atoms, preferably 2 to 8, 2 to 6, or 4 to 8 carbon atoms and more preferably 4 or 8 carbon atoms. $R^3$ is desirably a 2-ethylhexyl group or an n-butyl group.

Hindered, ester-substituted phenols can be prepared by heating a 2,6-dialkylphenol with an acrylate ester under base catalysis conditions, such as aqueous KOH.

EXAMPLE 9

To a 5-L round-bottomed 4-necked flask, equipped with a mechanical stirrer, thermal probe, and reflux condenser equipped for distillate removal, is charged 2619 g 2,6-di-t-butylphenol and 17.7 g potassium hydroxide (technical grade). The reaction mixture is heated to 135° C. over 35 minutes and maintained at temperature for 2 hours, removing 9.7 g aqueous distillate. To the reaction mixture is charged 1466 g butyl acrylate dropwise over the course of 90 minutes. The temperature is maintained at 135° C. for up to 2 hours, or until analysis by infrared indicates no further change (by observing peaks at 727 and 768 cm$^{-1}$). To the mixture is charged 103 g of a MgSiO$_4$ adsorbent, 17 g filter aid and stirring is continued for 2 hours, while removing 7.1 g distillate. The mixture is filtered through additional filter aid.

The compositions of the present invention may also include, or exclude, other components which are commonly found in lubricating compositions. For instance, corrosion inhibitors, extreme pressure agents, and anti-wear agents include but are not limited to chlorinated aliphatic hydrocarbons; boron-containing compounds including borate esters; and molybdenum compounds. Viscosity improvers include but are not limited to polyisobutenes, polymethyacrylate acid esters, polyacrylate acid esters, diene polymers, polyalkyl styrenes, alkenyl aryl conjugated diene copolymers, polyolefins and multifunctional viscosity improvers, including dispersant viscosity modifiers (which impart both dispersancy and viscosity improvement). Pour point depressants are a particularly useful type of additive, often included in the lubricating oils described herein usually comprising substances such as polymethacrylates, styrene-based polymers, crosslinked alkyl phenols, or alkyl naphthalenes,. See for example, page 8 of "Lubricant Additives" by C. V. Smalheer and R. Kennedy Smith (Lesius-Hiles Company Publishers, Cleveland, Ohio, 1967). Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162. These and other additives which may be used in combination with the present invention are described in greater detail in U.S. Pat. No. 4,582,618 (column 14, line 52 through column 17, line 16, inclusive) The effectiveness of the magnesium saligenin derivatives of the present invention, as opposed to known calcium saligenin derivatives, is reported in the following sets of differing formulations. The Ca saligenin derivative is prepared substantially as in Example 2 and is determined to contain 6 mole % aldehyde functionality content. The Mg saligenin derivative is prepared substantially as in Example The Volkswagen seal test involves immersing a number of specimens of cured Viton™ elastomer seal material in a sample of fluid to be tested and holding the samples at 150° C. for three 94-hour periods, replacing the test oil after the second 94 hour period. In this test the tension at break of the Viton™ seal after exposure (at 200 mm/min) is preferably at least 8 N/mm$^2$ and the elongation at break is preferably at least 160%. The seal preferably exhibits little or no cracking when tested by maintaining the specimen stretched to 100% elongation for 30 minutes.

The RBOT test is ASTM D-2272. The results are reported as time, in minutes, for oxygen pressure to decrease by 175 kPa (25.4 psi) from maximum pressure. Samples with higher oxidative induction time are superior, illustrating improved oxidative stability.

The Hot Tube Thermal Stability Test simulates deposit-forming tendencies in crankcase lubricants. A sample of lubricant is forced continuously at 285° C. through a small glass tube for 20 hours. At the conclusion of the test the deposits on the tube are visually evaluated for deposits. Higher ratings indicate less deposits (greater thermal stability).

|  | Formulation A | | Formulation B | | Formulation C | |
| --- | --- | --- | --- | --- | --- | --- |
| Example No. | C10 | 11 | C12 | 13 | C14 | 15 |
| Ca saligenin derivative, wt. % | 0.75 |  | 2.0 |  | 2.0 |  |
| Mg saligenin derivative |  | 0.75 |  | 2.0 |  | 2.0 |
| Base oil mixture: 240N + 100N RLOP oils (Group II oils) | X | X |  |  |  |  |
| 145N + 600N Esso oils (Group I oils) |  |  | X | X | X | X |
| Viscosity modifier mixture, wt. % | 8.2 | 8.2 | 6.8 | 6.8 | 1.0$^a$ | 1.0$^a$ |
| Ca sulfonate detergent(s), wt. % | 2.9 | 2.9 | 2.1 | 2.1 | 2.8 | 2.8 |
| S-containing Ca phenate detergent(s), wt. % | 1.0 | 1.0 | 1.6 | 1.6 | 1.9 | 1.9 |
| Copper corrosion test: p.p.m. Cu | 132 | 10 | 237 | 7 | 335 | 147 |
| VW Viton ™ seal test |  |  |  |  |  |  |
| mean final tensile strength | 7.6 | 9.5 | 6.6 | 6.5 | 7.4 | 8.8 |
| mean final elongation | 181 | 210.2 | 148.5 | 157.7 | 170.2 | 195.6 |
| cracking | mild | barely | moderate | mild | mild | barely |
| RBOT | 124 | 174 | n.d. | n.d. | n.d. | n.d. |
| Hot Tube Thermal Stability, rating | n.d. | n.d. | 61 | 83 | 83 | 83 | n.d. = not determined
$^a$Viscosity modifier for this formulation is supplied without diluent oil.

1 and is analyzed to have an aldehyde content of 31 mole %, a methylene bridge content of 31 mole %, an ether bridge content of 13 mole %, and a hydroxymethyl content of 25 mole %. In each of the pairs of examples within a formulation below, the composition remains constant except for the replacement of the Ca saligenin derivative with the Mg saligenin derivative. All amounts are presented inclusive of the diluent oil normally found in each component, unless otherwise noted. Other conventional additives which do not vary from one formulation to the next (dispersant, inhibitor, anti-foam and anti-wear agents) are not specifically listed.

The Examples are subjected to a series of 4 tests. The first is a copper corrosion test which involves immersing a copper coupon into a specimen of oil, heating the sample to 135° C., and blowing air through the heated sample for a defined number of hours. Lesser amounts of Cu detected in the samples after the test are better.

While the invention has been explained in relation to its preferred embodiments, it is to be understood that various modifications thereof will become apparent to those skilled in the art upon reading the disclosure. Therefore, it is to be understood that the invention disclosed herein is intended to cover such modifications as fall within the scope of the appended claims. Each of the documents referred to above is incorporated herein by reference. Except in the Examples, or where otherwise explicitly indicated, all numerical quantities in this description specifying amounts of materials, reaction conditions, molecular weights, number of carbon atoms, and the like., are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade.

However, the amount of each chemical component is presented exclusive of any solvent or diluent oil which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A composition comprising (A) a saligenin derivative represented by the formula wherein each X independently is —CHO, or —CH$_2$OH, each Y independently is —CH$_2$— or —CH$_2$OCH$_2$—, and wherein such —CHO groups comprise at least about 10 mole percent of the X and Y groups;

each M is independently hydrogen, ammonium, or a valence of a metal ion;

each R$^1$ is independently a hydrocarbyl group containing 1 to about 60 carbon atoms;

m is 0 to about 10; and each p is independently 0, 1, 2, or 3;

provided that at least one aromatic ring contains an R$^1$ substituent and that the total number of carbon atoms in all R$^1$ groups is at least 7;

further provided that if m is 1 or greater, then one of the X groups can be —H.

2. The composition of claim 1 wherein each M is independently Mg or H and the percentage of phenolic OH groups which are neutralized by Mg is about 10 to 100%.

3. The composition of claim 1 wherein the saligenin derivative is an overbased salt.

4. The composition of claim 3 wherein the saligenin derivative is an overbased magnesium or calcium salt or an overbased mixture of magnesium and calcium salts.

5. The composition of claim 4 wherein the overbased salt comprises a partially or fully neutralized magnesium salt which is overbased with a source of calcium ions.

6. The composition of claim 1 wherein R$^1$ is an alkyl group containing about 7 to about 28 carbon atoms.

7. The composition of claim 2 the phenolic OH groups are about 40% to about 90% neutralized by Mg.

8. The composition of claim 1 wherein m is about 2 to about 9.

9. The composition of claim 1 wherein the —CHO groups comprise at least about 15 mole percent of the X and Y groups.

10. The composition of claim 9 wherein the —CHO groups comprise about 20 to about 60 mole percent of the X and Y groups.

11. The composition of claim 1 wherein when X is at least in part —CH$_2$OH and such —CH$_2$OH groups comprise about 10 to about 50 mole percent of the X and Y groups.

12. The composition of claim 1 wherein when Y is at least in part —CH$_2$— and such —CH$_2$— groups comprise about 25 to about 55 mole percent of the X and Y groups.

13. The composition of claim 1 wherein when Y is at least in part —CH$_2$OCH$_2$— and such —CH$_2$OCH$_2$— groups comprise about 5 to about 20 mole percent of the X and Y groups.

14. The composition of claim 1 wherein (A) is treated with a borating agent.

15. A lubricating oil composition comprising a major amount of an oil of lubricating viscosity and a minor amount of the saligenin derivative (A) of claim 1.

16. The composition of claim 15 further comprising at least one of (B) a metal overbased composition other than overbased (A), (C) a dispersant, (D) a metal salt of a phosphorus acid, represented by the formula wherein R$^8$ and R$^9$ are each independently hydrocarbyl groups containing 3 to about 30 carbon atoms, M is a metal, and n is an integer equal to the valence of M, and (E) an antioxidant.

17. The composition of claim 16 wherein the metal overbased composition (B) is selected from the group consisting of (a) a metal overbased phenate derived from the reaction of an alkylated phenol wherein the alkyl group has at least about 6 aliphatic carbon atoms optionally reacted with an aldehyde or a sulfurization agent, or mixtures thereof, (b) a metal overbased sulfonate derived from an alkylated aryl sulfonic acid wherein the alkyl group has at least about 15 aliphatic carbon atoms, and (c) a metal overbased carboxylate derived from fatty acids having at least about 8 aliphatic carbon atoms.

18. The composition of claim 16 wherein the metal is calcium or magnesium.

19. The composition of claim 16 wherein the metal is lithium or sodium.

20. The composition of claim 17 wherein the metal overbased composition is treated with a borating agent.

21. The composition of claim 16 wherein the dispersant (C) comprises the reaction of a hydrocarbon substituted succinic acid-producing compound with at least about one-half equivalent, per equivalent of acid producing compound, of an organic hydroxy compound or an amine containing at least one hydrogen attached to a nitrogen atom, or a mixture of said hydroxy compound and amine.

22. The composition of claim 21 wherein the amine reacted with the succinic acid-producing compound is characterized by formula.

R$^4$R$^5$NH wherein R$^4$ and R$^5$ are each independently hydrogen, or hydrocarbon, amino-substituted hydrocarbon, hydroxy-substituted hydrocarbon, alkoxy-substituted hydrocarbon, amino, carbamyl, thiocarbamyl, guanyl, and acylimidoyl groups provided that only one of R$^4$ and R$^5$ is hydrogen.

23. The composition of claim 16 wherein (A) is treated with a borating agent.

24. The composition of claim 16 wherein the carboxylic dispersant composition (C) is treated with a borating agent.

25. The composition of claim 16 wherein the antioxidant is a material represented by the formula wherein $R^3$ is a straight chain or branched chain alkyl group containing 2 to about 22 carbon atoms.

26. The composition of claim 25 wherein the t-alkyl groups are t-butyl and $R^3$ contains 4 to 8 carbon atoms.

27. A process for preparing a saligenin derivative represented by the formula wherein each X independently is —CHO or —CH$_2$OH, each Y independently is —CH$_2$— or —CH$_2$OCH$_2$—;
each $R^1$ is independently a hydrocarbyl group containing 1 to about 60 carbon atoms;
(Mg) represents a valence of a magnesium ion;
each n is independently 0 or 1, the average value of n in the composition being about 0.1 to 1.0; provided that when n is 0, the Mg is replaced by H;
m is 0 to about 10;
and each p is independently 0, 1, 2, or 3;
provided that at least one aromatic ring contains an $R^1$ substituent and that the total number of carbon atoms in all $R^1$ groups is at least 7;
further provided that if m is 1 or greater, then one of the X groups can be —H;

said process comprising:
combining (a) a phenol substituted by said $R^1$ group with (b) formaldehyde or a source of formaldehyde, and (c) and magnesium oxide or magnesium hydroxide, under reactive conditions in the presence of a catalytic amount of a strong base;
wherein the equivalent ratio of the substituted phenol to formaldehyde or source thereof is about 1:1 to about 1:4;
whereby said saligenin derivative is formed such that X is at least in part —CHO and such —CHO groups comprise at least about 10% of the X and Y groups.

28. The process of claim 27 wherein the strong base is sodium hydroxide or potassium hydroxide.

29. The process of claim 27 wherein the equivalent ratio of the substituted phenol to formaldehyde or source thereof is about 1:1.1 to about 1:2.9.

30. The process of claim 27 wherein the process is conducted in the substantial absence of added solvent.

31. The process of claim 27 wherein the reaction mixture is heated to a final temperature of about 100 to about 150° C.

32. A process for preparing an overbased saligenin derivative, comprising adding to the product of claim 27 an excess of a basic metal compound and adding thereto a gaseous acidic material under conditions to react with the majority of the stoichiometric excess of the metal base.

33. The process of claim 32 wherein the metal of said basic metal compound is magnesium.

34. The process of claim 32 wherein said metal is calcium.

35. The process of claim 32, wherein a surfactant is additionally present.

36. The process of claim 32 wherein the product is further treated with a borating agent.

* * * * *